US008503613B2

(12) United States Patent
Sabol et al.

(10) Patent No.: US 8,503,613 B2
(45) Date of Patent: Aug. 6, 2013

(54) DOSE LEVEL INDICATION (75) Inventors: John Michael Sabol, Sussex, WI (US); Rowland Frederick Saunders, Hartland, WI (US); Jon Charles Omernick, Wauwatosa, WI (US); Kadri Nizar Jabri, Oak Creek, WI (US); Christopher Aaron Paulik, Menomonee Falls, WI (US); François Hensen, Delafield, WI (US); Bruce Alan Bergendahl, Delafield, WI (US)

(73) Assignee: General Electric Company, Schenectady, NY (US)

( * ) Notice: Subject to any disclaimer, the term of this patent is extended or adjusted under 35 U.S.C. 154(b) by 289 days.

(21) Appl. No.: 12/953,811

(22) Filed: Nov. 24, 2010

(65) Prior Publication Data
US 2012/0128116 A1    May 24, 2012

(51) Int. Cl.
*H05G 1/64* (2006.01)

(52) U.S. Cl.
USPC ........................................ 378/98.5; 378/165

(58) Field of Classification Search
USPC ...................... 378/4, 98, 98.2, 98.5, 108, 165
See application file for complete search history.

(56) References Cited

U.S. PATENT DOCUMENTS

| 7,103,139 | B2 * | 9/2006 | Nagaoka et al. ................ 378/16 |
| 7,742,572 | B2 * | 6/2010 | Inuga et al. .................... 378/108 |
| 7,801,273 | B2 | 9/2010 | Hoornaert et al. |
| 2006/0193437 | A1 | 8/2006 | Boeing et al. |
| 2009/0074143 | A1 | 3/2009 | Tsukagoshi et al. |

FOREIGN PATENT DOCUMENTS

| EP | 1990005 A1 | 11/2008 |
| JP | 2009172138 A | 8/2009 |

OTHER PUBLICATIONS

Search Report and Written Opinion from corresponding PCT Application No. PCT/US2011/059035 dated Jan. 26, 2012.
"Quantities and Units for Measurement and Calculation in Medical X-Ray Imaging", Journal of the ICRU, vol. 5, No. 2, Report 74 (2005), Chapter 3, pp. 25-34.

* cited by examiner

*Primary Examiner* — Jurie Yun
(74) *Attorney, Agent, or Firm* — Fletcher Yoder, P.C.

(57) ABSTRACT

Providing an operator with information concerning radiation dose associated with an imaging operation is disclosed. In certain embodiments, the dose information may be provided in conjunction with indicators related to reference dose levels to facilitate evaluation of the dose in the context of the reference levels. The dose information may be based on real-time assessment of dose or may be an expected dose based on a proposed or planned sequence of exposure events. Further the indication may be prospective, providing an indication to the operator of when certain dose thresholds may be crossed.

21 Claims, 9 Drawing Sheets

DOSE LEVEL INDICATION

BACKGROUND OF THE INVENTION

The subject matter disclosed herein relates generally to the monitoring of radiation dose in an imaging context.

In the field of medical imaging, various types of imaging are based upon the differential or attenuated passage of radiation through a patient to generate an image of the internal features of the patient. That is, the patient is exposed to a source of radiation and the radiation that passes through the patient is detected and used to generate useful images of the internal organs or structures within the patient.

Thus, when such imaging technologies are employed, part of the imaging process involves exposing the patient to some dose of radiation. Depending on the type of imaging being performed, the radiation dose may be fixed (such as where the imaging process involves exposing the patient to X-rays of a specified energy for a specified time) or unfixed (such as where a number of low-energy images are obtained over an unspecified amount of time to assist in an interventional procedure). Typically the radiation dose to which the patient is exposed is regulated by governmental or hospital guidelines. However, even in situations where the dose is within established guidelines or where such guidelines do not apply, it may be desirable for a practitioner to have greater knowledge of the radiation dose to which the patient is exposed.

BRIEF DESCRIPTION OF THE INVENTION

With the foregoing considerations in mind, the present disclosure relates generally to providing indications to an operator of ongoing or anticipated dose to which a patient is exposed. The indication may be provided in conjunction with a corresponding reference dose level to facilitate evaluation of the dose in the context of the reference level. The indication may be based on real-time (i.e., current or contemporaneous) assessment of dose or may be an expected dose based on a proposed or planned sequence of exposure events. Further the indication may be prospective, providing an indication to the operator of when certain dose thresholds may be crossed.

In one embodiment, a method for conveying radiation dose information is provided. The method includes the act of determining an accumulated dose of radiation to which a patient is exposed during an imaging operation. A visual indication of the accumulated dose of radiation and a visual indication of one or more reference dose levels is displayed. The display of the visual indication of the accumulated dose of radiation relative to the reference levels is updated if the accumulated dose of radiation changes.

In a further embodiment, a method for conveying radiation dose information is provided. The method includes the act of estimating a dose of radiation to which a patient will be exposed based on a proposed set of image acquisitions. A visual indication of the estimate of the dose along with a visual indication of one or more reference dose levels is displayed. The display of the visual indication of the estimate of the dose of radiation is updated in response to changes made to the proposed set of image acquisitions.

In an additional embodiment, an imaging system is provided. The imaging system includes a source of radiation and a detector on which radiation emitted by the source is detected and converted to signals. Also provided is a system controller controlling operation of one or both of the source and the detector and a workstation in communication with the system controller. The workstation is configured to display images reconstructed from the signals; a visual indication of a dose of radiation administered during an imaging operation performed by the imaging system; and a visual indication of one or more reference dose levels.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein.

DETAILED DESCRIPTION OF THE INVENTION

The present disclosure relates to approaches that may be utilized to provide feedback concerning radiation dose and any relevant reference dose levels, to an operator of an imaging system. In certain embodiments, the feedback may be provided in substantially real-time or in a dynamic fashion so that the operator may take radiation dose into account in an ongoing imaging session. Alternatively, in other embodiments where dose is essentially fixed for different imaging protocols, a series or sequence of proposed imaging operations may be evaluated to provide the operator with the potential dose information prior to initiating the imaging session. In this manner, the operator may adjust the proposed imaging sequence to account for the dose which would be incurred. In addition, in certain embodiments, the time at which certain dose thresholds might be exceeded is provided to the operator, allowing the operator to make adjustments to an ongoing imaging session. Likewise, in other implementations, dose information as it pertains to specific portions of the patient may be provided, allowing the operator to evaluate the dose to the extent that the dose is distributed or concentrated on specific body parts.

As used herein, the term "dose" or "dosage" encompasses a variety of concepts. For example, in its most basic sense the term "dose" may equate to the absorbed dose, D, which quantifies the deposition of energy by ionizing radiation, typically as the quotient of the mean energy imparted to matter having a specified mass. Under conditions typically found in medical imaging, the absorbed dose is numerically equivalent to kerma, K, which relates to the kinetic energy of all charged particles liberated by uncharged particles and is quantified as the quotient of the sum of the initial energies of all charged particles liberated by uncharged particles in matter having a specified mass. The absorbed dose (or equivalent kerma) may also be considered in view of a specified time frame to yield an absorbed dose rate. With this basic framework in mind, dose or dosage indications as discussed herein may encompass a variety of dosimetric quantities and/or rates as known and used in the art, including, but no limited to: incident air kerma, incident air kerma rate, entrance-surface air kerma, entrance-surface air kerma rate, air kerma-area product, air kerma-area product rate, and air kerma-length product. Of these listed examples, incident air kerma, incident air kerma rate, entrance-surface air kerma, entrance-surface air kerma rate, air kerma-area product, and air kerma-area product rate may be most suitable in the context of radiography and fluoroscopy while air kerma-length product may be most suitable in the context of computed tomography (CT). In addition, dose or dosage indications as discussed herein may encompass a variety of risk-adjusted or risk-related dosimetric quantities as known and used in the art, including, but no limited to: organ dose (i.e., absorbed dose for specific organs or tissues), equivalent dose (i.e., the present weighted absorbed dose), and effective dose (i.e., the sum of the weighted equivalent doses in all of the tissues and organs of the body). Thus, the terms "dose" or "dosage" as used herein may generally encompass a variety of medically useful dosimetric quantities or rates as well as risk-related dosimetric quantities or rates. Further, in certain embodiments, a user or operator may specify or customize what measure of dose is calculated (or estimated) and displayed, as discussed herein.

Figure 1:
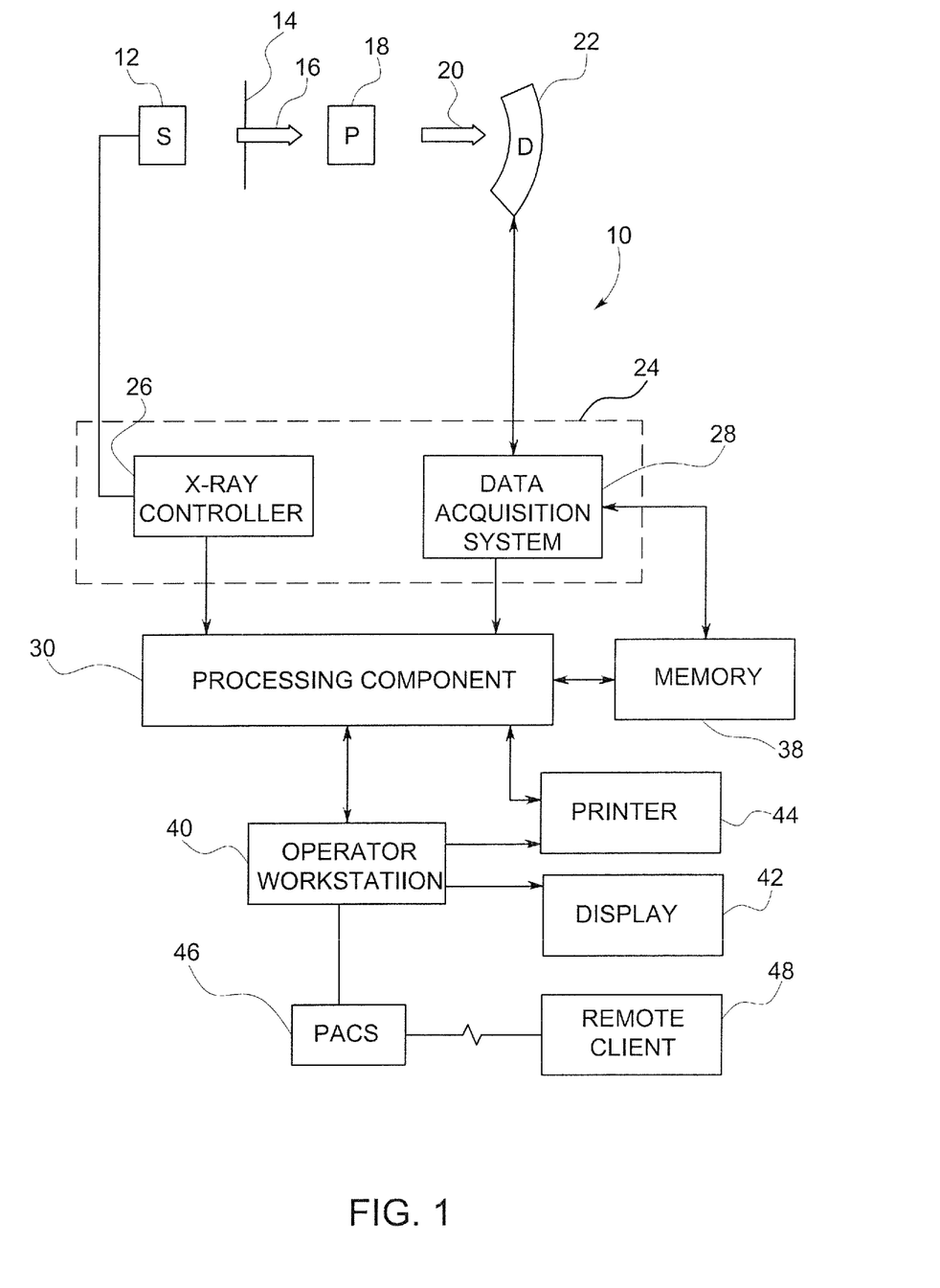
FIG. 1 depicts an imaging system for use in providing radiation dose information in accordance with aspects of the present disclosure.

With the foregoing in mind, an example of an X-ray based imaging system 10 suitable for generating and providing such dose information is provided in FIG. 1. The X-ray based imaging system 10 may be one of a variety of different imaging modalities that generate X-rays and collect data related to the attenuation of such radiation by a patient. Based on the collected data, images may be generated that depict internal features of the patient 18. Examples of suitable imaging systems 10 include, but are not limited to, conventional radiography, tomosynthesis, C-arm angiography, mammography, computed tomography (CT), and so forth.

In the embodiment illustrated in FIG. 1, imaging system 10 includes a source of X-ray radiation 12 which may, in certain embodiments, be positioned adjacent to a collimator 14. The collimator 14, when present, shapes the beam of emitted X-rays 16 to limit the area exposed to the X-ray 16. A portion of the X-ray radiation 20 passes through or around the patient 18 and impacts a detector array, represented generally at reference numeral 22. Detector elements of the array produce electrical signals that represent the intensity of the incident X-rays 20. These signals are acquired and processed to reconstruct images of the features within the patient 18.

The source 12 is controlled by a system controller 24, which furnishes both power, and control signals based on the specified imaging protocol or as otherwise specified by an operator. In the depicted embodiment, the system controller 24 controls the source 12 via an X-ray controller 26 which may be a component of the system controller 24. In such an embodiment, the X-ray controller 26 may be configured to provide power and timing signals to the X-ray source 12.

Moreover, the detector 22 is coupled to the system controller 24, which controls acquisition of the signals generated in the detector 22. In the depicted embodiment, the system controller 24 acquires the signals generated by the detector using a data acquisition system 28. The data acquisition system 28 receives data collected by readout electronics of the detector 22. The data acquisition system 28 may receive sampled analog signals from the detector 22 and convert the data to digital signals for subsequent processing by a processor 30 discussed below. Alternatively, in other embodiments the digital-to-analog conversion may be performed by circuitry provided on the detector 22 itself. The system controller 24 may also execute various signal processing and filtration functions with regard to the acquired image signals, such as for initial adjustment of dynamic ranges, interleaving of digital image data, and so forth.

In certain embodiments in which the source 12 and/or detector 22 are configured to move and/or rotate relative to the patient 18, other features may be present to facilitate such motion and/or rotation. These features, such as a rotational subsystem and a linear positioning subsystem, may also be controlled via the system controller 24, such as by a motor subsystem of the controller 24. In these embodiments, rotation of a gantry or C-arm about the patient 18 may be controlled and/or the linear movement of a support or table on which the patient 18 rests may be controlled.

In general, system controller 24 commands operation of the imaging system 10 (such as via the operation of the source 12, detector 22, and positioning systems described above) to execute examination protocols and to process acquired data. In the present context, the system controller 24 may also include signal processing circuitry as well as associated memory circuitry for storing configuration parameters, image data, and programs or routines executed by the computer (such as routines for dose information as described herein).

In the depicted embodiment, the image signals acquired and processed by the system controller 24 are provided to a processing component 30 for reconstruction of images. The processing component 30 may be one or more conventional microprocessors. The data collected by the data acquisition system 28 may be transmitted to the processing component 30 directly or after storage in a memory 38. Any type of memory suitable for storing data might be utilized by such an exemplary system 10. For example, the memory 38 may include one or more optical, magnetic, and/or solid state memory storage structures. Moreover, the memory 38 may be located at the acquisition system site and/or may include remote storage devices for storing data, processing parameters, and/or routines for image processing and display.

The processing component 30 may be configured to receive commands and scanning parameters from an operator via an operator workstation 40, typically equipped with a keyboard and/or other input devices. An operator may control the system 10 via the operator workstation 40. Thus, the operator may observe the reconstructed images, observe estimated or measured dose information, and/or otherwise operate the system 10 using the operator workstation 40. For example, a display 42 coupled to the operator workstation 40 may be utilized to observe the reconstructed images, to monitor patient dose, and/or to control imaging. Additionally, the images may also be printed by a printer 44 which may be coupled to the operator workstation 40.

Further, the processing component 30 and operator workstation 40 may be coupled to other output devices, which may include standard or special purpose computer monitors and associated processing circuitry. One or more operator workstations 40 may be further linked in the system for outputting system parameters, requesting examinations, monitoring patient dose, viewing images, and so forth. In general, displays, printers, workstations, and similar devices supplied within the system may be local to the data acquisition components, or may be remote from these components, such as elsewhere within an institution or hospital, or in an entirely different location, linked to the image acquisition system via one or more configurable networks, such as the Internet, virtual private networks, and so forth.

It should be further noted that the operator workstation 40 may also be coupled to a picture archiving and communications system (PACS) 46. PACS 46 may in turn be coupled to a remote client 48, radiology department information system (RIS), hospital information system (HIS) or to an internal or external network, so that others at different locations may gain access to the raw or processed image data.

While the preceding discussion has treated the various exemplary components of the imaging system 10 separately, these various components may be provided within a common platform or in interconnected platforms. For example, the processing component 30, memory 38, and operator workstation 40 may be provided collectively as a general or special purpose computer or workstation configured to operate in accordance with the present disclosure. In such embodiments, the general or special purpose computer may be provided as a separate component with respect to the data acquisition components of the system 10 or may be provided in a common platform with such components. Likewise, the system controller 24 may be provided as part of such a computer or workstation or as part of a separate system dedicated to image acquisition.

Figure 2:
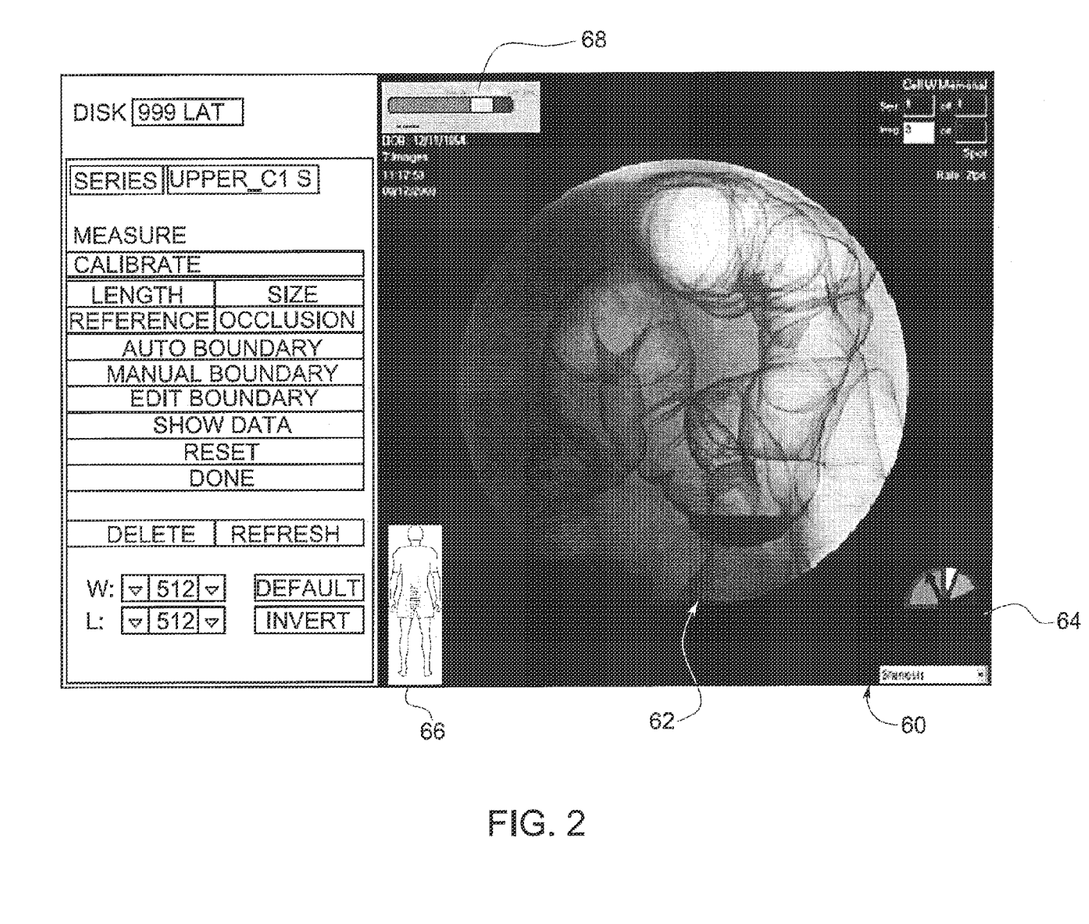
FIG. 2 depicts a screen that includes a variety of dose-indicators, in accordance with aspects of the present disclosure.

With the foregoing example of one suitable image acquisition system in mind, one or more approaches for notifying an operator of the dose being applied to a patient are discussed. For example, in one embodiment, the system 10 discussed above may be used to apply a sequence or series of pre-defined imaging protocols to a patient (such as in the context of CT) or may be used to acquire an ongoing series of images for the duration of an interventional or surgical procedure (such as in the context of fluoroscopy). Turning now to FIG. 2, one example of a screen 60 that may be displayed to an operator prior to or during the course of an imaging session is depicted. In this example, a reconstructed image 62 obtained using an X-ray based imaging modality is displayed. In addition, a variety of dose indicators 64, 66, 68 are displayed that provide information about the dose experienced by the patient 18 (FIG. 1). In these various examples, depending on the imaging modality being employed, the visual indicators may be used to indicate a current dose level (such as in a fluoroscopy context where images are acquired in an open-ended, ongoing process) or a projected or expected dose level (such as in a CT context where a series of defined imaging protocols may be executed which will result in an aggregate or combined dose being applied to the patient). In certain embodiments, the reference levels or information conveyed by one or more of the visual indicators may be customized by the operator. That is the operator may specify what reference dose levels are of interest and/or are displayed.

Figure 3:
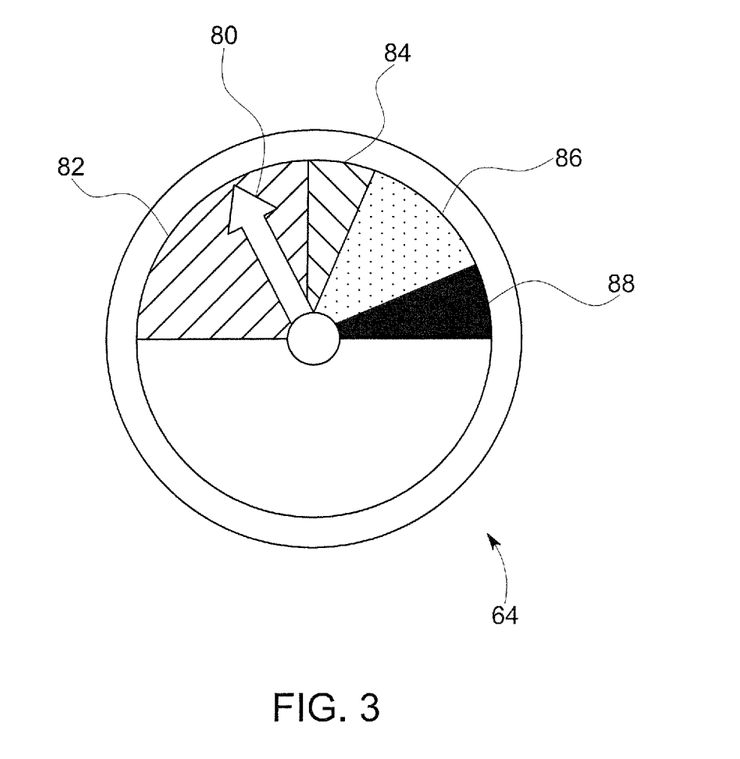
FIG. 3 depicts an example of one embodiment of a dose indicator, in accordance with aspects of the present disclosure.

One example of a dose indicator is provided in the form of a virtual gauge 64, as depicted in greater detail in FIG. 3. As will be appreciated, other virtual representations may be used to achieve the same effect as the virtual gauge, i.e., providing a visual indication of current or accumulated radiation dose along with one or more reference levels that provide context for the current dose. In the various embodiments discussed herein, the accumulated dose level may be based on actual measurement or on a current calculation or estimation based on a priori assumptions and/or numerical or statistical models. In the depicted implementation a virtual needle 80 may depict a current or accumulated dose level, such as within an acceptable or expected zone 82. Likewise a zone 84 that exceeds a warning level may be displayed such that when the needle 80 points to this zone 84, the operator is informed that the dose has exceeded the warning level.

Likewise, further degrees of warning or reference may also be provided. For example, a zone 86 that exceeds a reference level may, when pointed to by needle 80, indicate that the dose has exceeded the level associated with a mere warning. Likewise, a zone 88 may be displayed that corresponds to dose levels associated with reportable events. Thus, the zones 84, 86, and 88 may represent progressively greater levels of radiation dose and may each be associated with a greater degree of caution or with specified procedures or actions (such as, ultimately, the reporting of an excessive dose exposure event). Based on the current displayed dose level and the indicated reference levels, an operator can modify the imaging activity (such as the rate at which fluoroscopic images are acquired) to keep dose levels within acceptable bounds. As will be appreciated, the virtual gauge 64 (or corresponding virtual indication) may be displayed using different colors or shading to more effectively convey the current dose and reference level information to a viewer.

In other embodiments, other or additional dose information may be conveyed to the viewer. For example, turning to FIG. 4, a representation of a human form 66 may be displayed on which dose information is superimposed to indicate the distribution 90 of dose across different anatomic regions of the patient 18. In this example, stippling, color, or shading may be used to indicate what portions of the body of the patient have been exposed to radiation and the respective dose of radiation to which each of these portions has been exposed. For example, in an implementation where color or stippling is used to indicate the radiation dose on a body part, a greater intensity of color or density of stippling may correspond to greater levels of dose.

Figure 4:
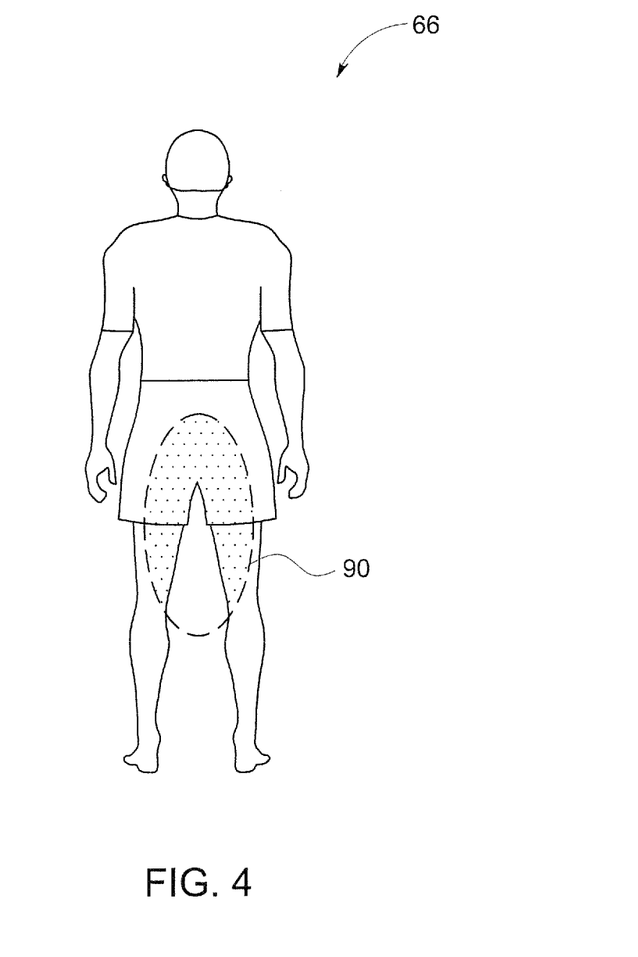
FIG. 4 depicts an example of a further embodiment of a dose indicator, in accordance with aspects of the present disclosure.

Based on this indication of dose distribution with respect to the patient, the operator can modify the imaging activity (such as the rate at which fluoroscopic images are acquired and/or the placement or orientation of the patient with respect to the source/detector geometry) to keep dose levels within acceptable bounds for the exposed body parts. That is, the imaging process may be dynamically adjusted or controlled based on the displayed dose information. As the operator adjusts the image acquisition process, the current or cumulative distribution of dose with respect to the body of the patient may be recalculated and an updated dose distribution displayed.

In embodiments employing a visual indicator where dose information is depicted in the context of the affected regions of the body, information about the imaging geometry, the placement of the patient, and/or the imaging protocol being employed may be provided by the operator so that the affected body parts can be properly depicted with respect to the current or projected dose information. Further, in other embodiments such information may be derived based on user feedback or interaction with the reconstructed image 62, such as by selecting and labeling particular body parts.

Figure 5:
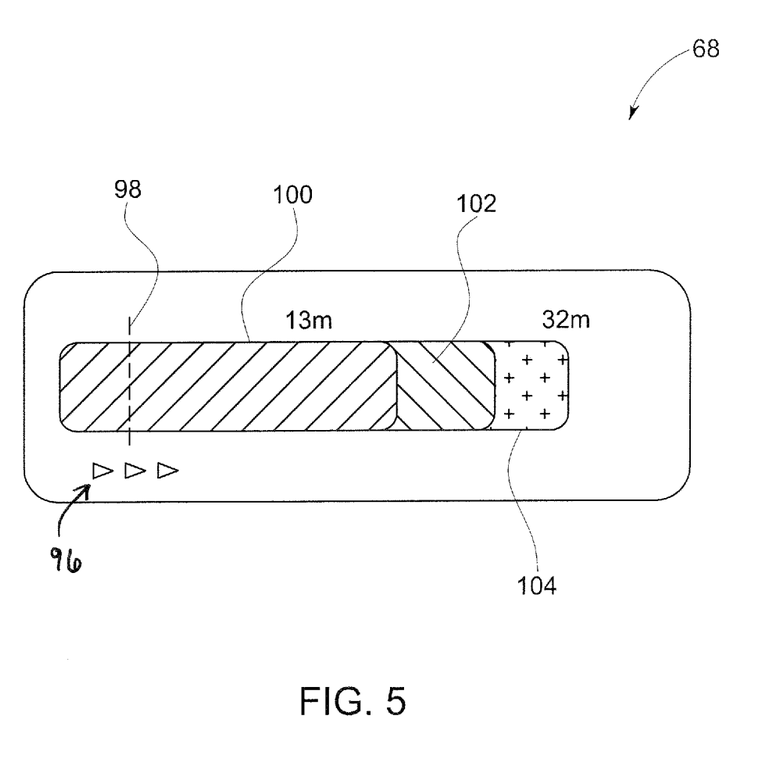
FIG. 5 depicts an example of another embodiment of a dose indicator, in accordance with aspects of the present disclosure.

Turning to FIG. 5, in a further implementation, a timeline visual indicator 68 may be provided. In the depicted example, the timeline visual indicator 68 includes an indication 98 of current dose in the context of a timeline that displays when various reference dose levels may be exceeded based on current or projected exposure rates. In such an embodiment, the indication 98 of current dose may be a real-time or substantially real-time indication of the current dose experienced by the patient (e.g., current to within one or two seconds or less). For example, in the depicted example, different zones 100, 102, 104 corresponding to different thresholds levels (e.g., a warning level, a reference level, a reportable dose event level) are depicted in a longitudinal arrangement that is traversed by the dose indication 98 as the patient 18 is exposed to radiation. In this example, each zone 100, 102, 104, may be color-coded or shaded so that a viewer can readily ascertain where along the reference spectrum the current dose indication 98 lies.

In addition, in the depicted embodiment, an indicator 96 may be provided that conveys the rate, in a relative or absolute sense, at which dose is being accumulated by the patient. For example, in the depicted example, a series of arrows are displayed as the indicator 96 to convey the rate at which dose is accumulating. In this example, fewer arrows would signify a lower rate of dose accumulation while more arrows would signify a greater rate of dose accumulation. Further, the indicator 96 may be color-coded or shaded to convey additional information about the rate of exposure. For example, green arrows may indicate a low rate of exposure, yellow arrows may indicate a moderate rate of exposure, and red arrows may indicate a relatively high rate of exposure. In addition, in certain embodiments a numerical value may be provided in the appropriate units, to provide an absolute indication of the rate at which dose is accumulated. Such an absolute indication may be provided in addition to or in place of a relative indication of dose rate.

Further, in the depicted example the estimated time remaining, such as based on an average, expected, or projected exposure rate, is displayed in conjunction with each zone 100, 102, 104 so that the viewer can ascertain at what time the current or projected dose will exceed a given threshold. Based on this indication of time remaining and/or on the location of the dose indication 98 with respect to the displayed threshold levels, the operator can modify the imaging activity (such as the rate at which fluoroscopic images are acquired) to keep dose levels within acceptable bounds. That is, the imaging process may be dynamically adjusted or controlled based on the displayed dose information. As the operator adjusts the image acquisition process (such as the at which rate images are acquired) the time remaining associated with each threshold may be recalculated and new values displayed.

Figure 6:
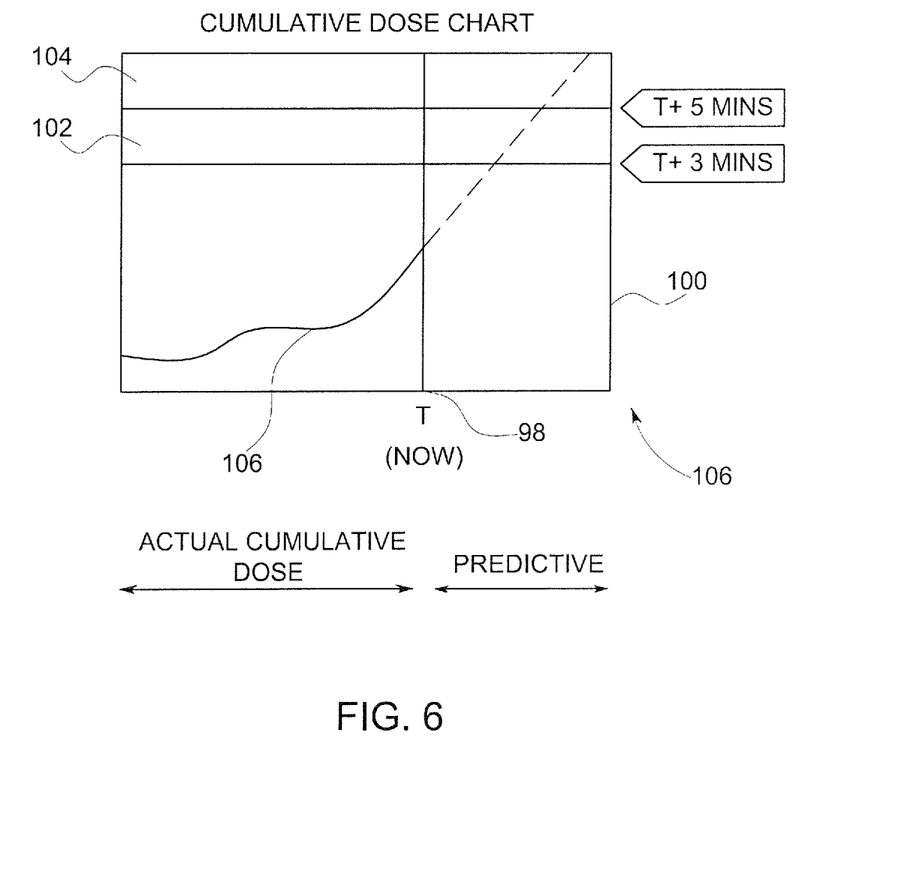
FIG. 6 depicts an example of an additional embodiment of a dose indicator, in accordance with aspects of the present disclosure.

Turning to FIG. 6, another implementation of a time-based indicator 106 is depicted. In this implementation, the cumulative dose 108 is graphically depicted along with a time line 110. The intersection of the time line 110 and the cumulative dose 108 indicates the dose acquired up to time T. In the depicted example, accumulated dose (i.e., dose accumulated up to time T) is depicted by a solid line while projected dose at future times is depicted by a dotted line. In this example, different zones (which may be graphically depicted using different color or shading) 100, 102, 104 are depicted along the vertical axis. As in previous examples, the different zones may correspond to different respective thresholds levels (e.g., a warning level, a reference level, a reportable dose event level, and so forth). Thus, in this example, as dose is accumulated, the time line 110 may move to the right and the cumulative dose, as represented by line 108 may move upward and toward the right to indicate the approach of the cumulative dose to the different threshold levels.

Based on the observed or expected rate of dose accumulation, one or more indications may be displayed that indicate the projected time remaining prior to the cumulative dose exceeding a specified reference or threshold level (such as a warning or reporting level). As in the preceding example, based on these indications an operator may make adjustments to the image acquisition process based on these time remaining indications. As the operator adjusts the image acquisition process (such as the rate at which images are acquired) the time remaining associated with each threshold may be recalculated and new values displayed. Likewise, as adjustments to the imaging process are made, the projected or predicted cumulative dose (represented by the dashed portion of line 108) may change and the recalculated line displayed to reflect the new prediction.

Figure 7:
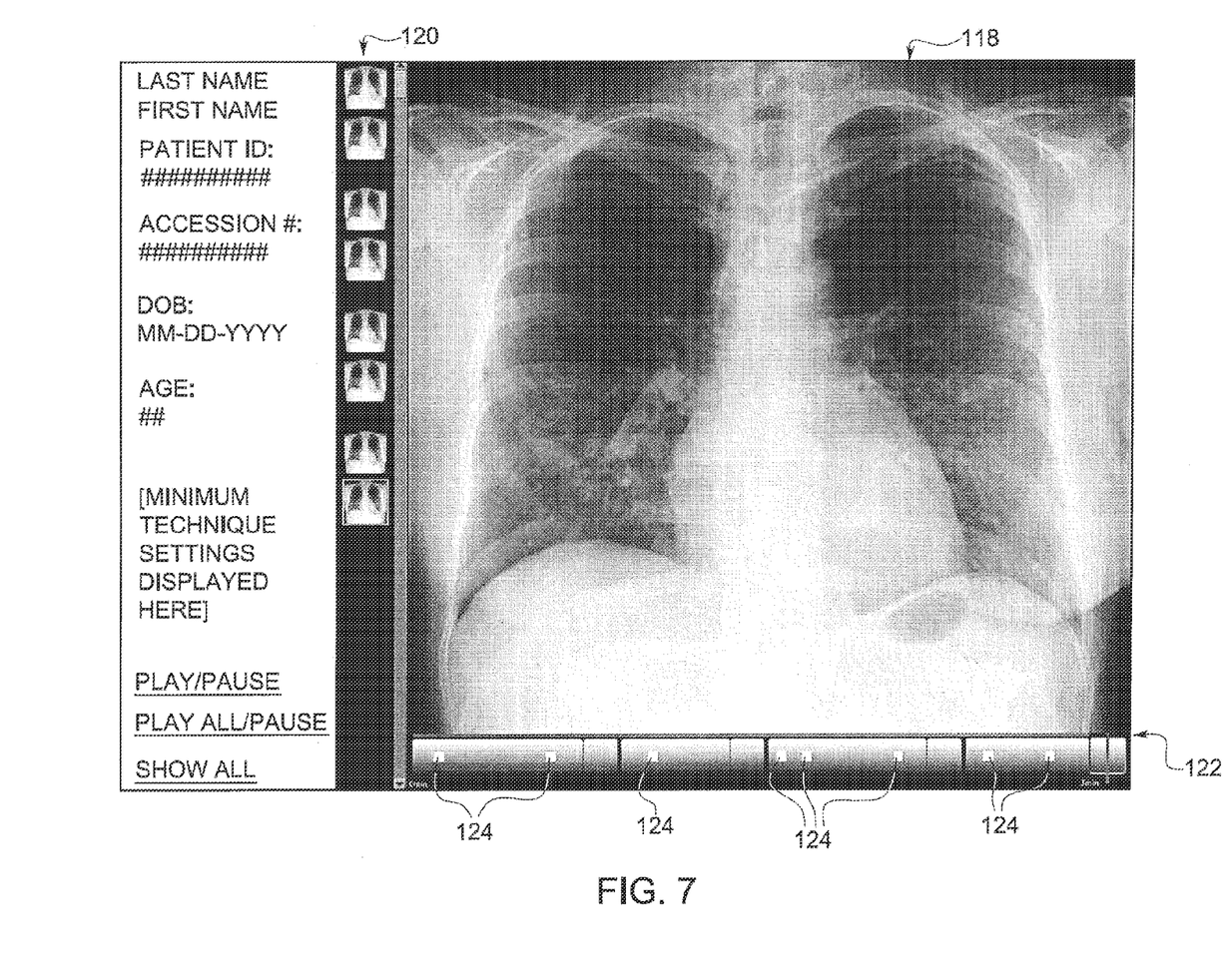
FIG. 7 depicts a screen that includes a dosage timeline, in accordance with aspects of the present disclosure.

Turning to FIG. 7, another timeline related example is provided in the context of a fluoroscopic acquisition, in which a series of low-energy images are acquired over an extended, open-ended period, such as during an interventional procedure or surgical operation. Because the time associated with the fluoroscopic image acquisition process is typically open-ended, the images are acquired in an ongoing manner which may be based on a fixed period (e.g., every 10 seconds, 30 seconds, 1 minute, 2 minutes, and so forth) and/or based on events or operator control (e.g., based on milestones associated with the corresponding interventional procedure or based on the operator manually causing the acquisition of an image).

In the depicted example, a screen 118 displays a selected image along with a sequence 120 of thumbnail images representing some or all of the acquired fluoroscopic images. An image displayed in the main portion of the screen 118 may correspond to the thumbnail image selected in the displayed sequence 120. In addition, in the depicted example a timeline is displayed along the bottom depicting image acquisition events 124 over time. In this example, the series of depicted acquisition events 124 corresponds to the series of depicted thumbnail images in the displayed sequence 120.

In the depicted example, a dose indicator 122 may be displayed that is color-coded or shaded and/or that includes a dose indication line or bar. In an ongoing imaging process, such as fluoroscopy, the dose indicator may change color or shading and/or an indicator line, if present, may move to indicate the accumulation of dose. In one embodiment, as reference or threshold levels are exceeded, the color or shading may change (such as from green to yellow to red) and/or the line indicator may be moved so as to visually indicate to the viewer that a threshold dose level has been exceeded. In one such embodiment, the location of the transition would shift on the timeline to match or otherwise indicate the point in the imaging process where the transition occurred, i.e., where the reference level was exceeded. In this manner, a viewer may relate each acquisition event 124 with a corresponding cumulative dose. As in previous embodiments, based on this information, the operator may make adjustments to the image acquisition process, if is still ongoing, based on the displayed dose information.

While fluoroscopy provides an example where the ultimate dose to the patient is unknown until the image acquisition process is complete, in other modalities the dose to the patient may be determinable before the imaging procedure is initiated. For example, in CT and radiography each imaging protocol (or combination of protocols) may expose the patient to a known and fixed dose of radiation or an accumulation of known, fixed doses. In such implementations, it may be useful to provide an operator with an indication (based on a selected imaging protocol or sequence of protocols and the imaging parameters associated with each protocol) of how much dose the patient will accumulate if images are acquired as configured and of how this accumulated dose compares to reference levels of interest.

Figure 8:
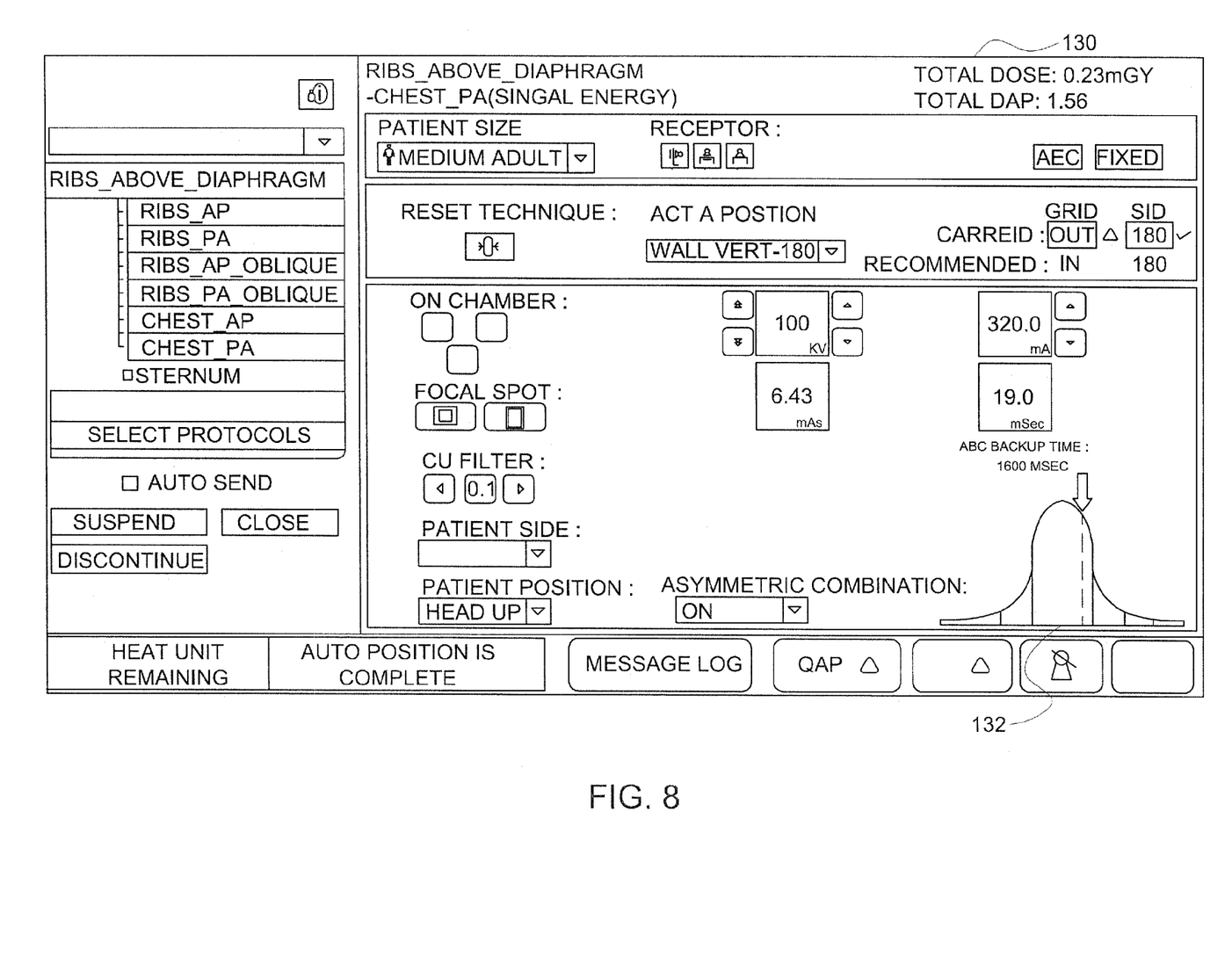
FIG. 8 depicts a screen that includes a dose-indicators, in accordance with aspects of the present disclosure.
Figure 9:
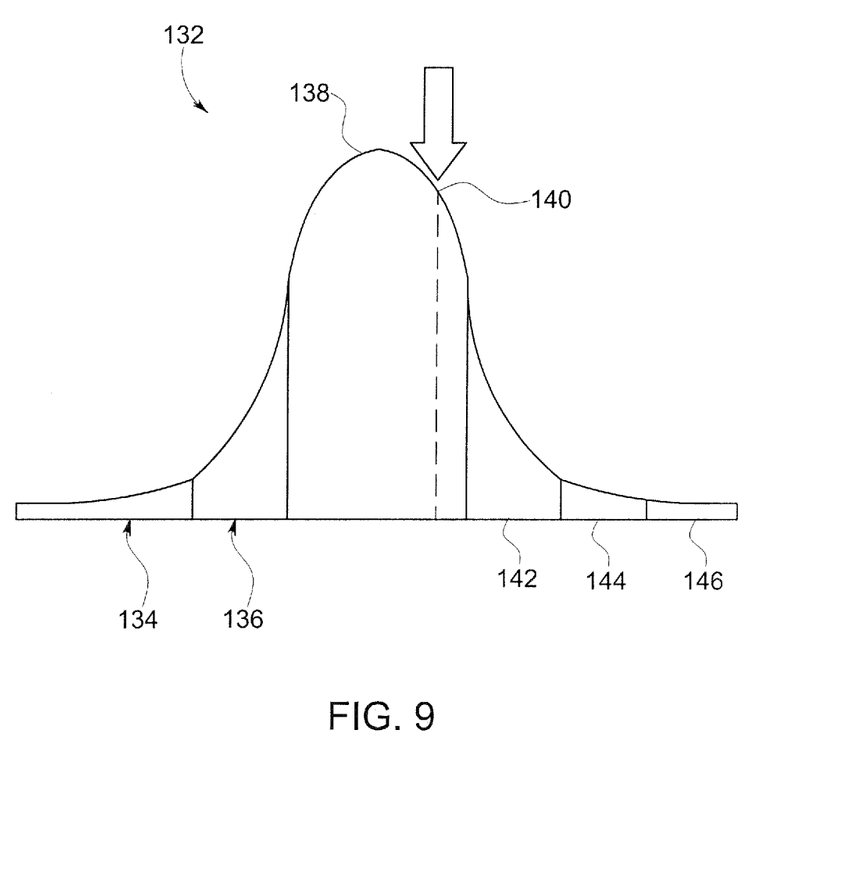
FIG. 9 depicts an example of one embodiment of a dose indicator, in accordance with aspects of the present disclosure.

To this end, and turning to FIGS. 8 and 9, a setup screen 130 for implementing an image acquisition session may include a projected dose indication 132 that includes reference levels of interest to the operator. For example, in the depicted implementation, the estimated dose for the procedure may be represented by a line 140 or other suitable indicator (such as the depicted arrow). This dose indicator may be displayed as part of the projected dose indication 132 which may also include a reference curve or other graphic for displaying one or more dose reference levels in conjunction with the projected dose line 140.

For example, in the depicted implementation, the reference curve is broken into six different zones that may be of interest to an operator. For example, the target zone 138 may represent the dose range where the projected dose is deemed to be acceptable. To the right of the target zone 138, in the direction of increasing dose, a high dose warning zone 142 may represent a dose level that is above the target range 138 but below a reference dose level, represented by zone 144. Likewise, the reference dose level may be below the dose level associated with a reportable dose event, represented by zone 146.

In this example, on the other side of the target zone 138 in the direction of decreasing dose, a low dose warning zone 142 may represent a dose level that is below the target range 138 but still deemed suitable for image acquisition purposes. Below the low dose warning zone 142 may be an extreme low dose warning zone 134 at which image quality is impaired. Thus, based on the projected dose line 140 and where this line falls within the reference curve, an operator may make adjustments prior to beginning an imaging process to optimize the dose to which the patient is exposed while obtaining images of acceptable quality. For example, the operator may add or remove certain imaging acquisition steps from the proposed acquisition sequence, or may alter one or more parameters associated with some or all of the image acquisition steps, such as the exposure duration, the collimation applied to the beam of X-rays (i.e., the exposure area), the energy level associated with the X-rays, the rotational speed of the gantry, the translation speed of the patient support, and so forth.

Technical effects of the invention include calculating and/or displaying an indication of a dose level to which a patient has been exposed or will be exposed as part of an imaging process. The projected or measured dose level may be displayed as part of an image acquisition process so that an operator may adjust the imaging process, prior to or during image acquisition, based on the displayed dose information. A further technical effect of the invention, in certain embodiments, is the use of circuitry in an imaging system to calculate and display an accumulated dose during an ongoing imaging procedure so that an operator may modify the ongoing image acquisition based on the dose information.

This written description uses examples to disclose the invention, including the best mode, and also to enable any person skilled in the art to practice the invention, including making and using any devices or systems and performing any incorporated methods. Aspects or features of examples provided herein may be combined or mixed with aspects or features of other examples without deviating from the scope of the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A method for conveying radiation dose information comprising:
    determining an accumulated dose of radiation to which a patient is exposed during an ongoing imaging operation;
    displaying a visual indication of the accumulated dose of radiation as the dose of radiation is accumulated and a visual indication of one or more reference dose levels; and
    updating the display of the visual indication of the accumulated dose of radiation relative to the reference levels if the accumulated dose of radiation changes.

2. The method of claim 1 comprising displaying an estimate of time remaining until the accumulated dose of radiation exceeds one of the one or more reference dose levels.

3. The method of claim 1 comprising displaying an estimated total dose of radiation based on expected radiation exposure.

4. The method of claim 1 comprising receiving one or more user inputs modifying an ongoing image acquisition process based on the displayed visual indication of the accumulated dose and the visual indication of one or more reference dose levels.

5. The method of claim 1 comprising receiving one or more user inputs modifying an ongoing image acquisition process based on an estimate of time remaining before a reference dose level is exceeded.

6. The method of claim 1 wherein the visual indication of the accumulated dose and the visual indication of one or more reference dose levels are displayed in conjunction with one or more reconstructed images generated during the ongoing imaging operation.

7. The method of claim 1 wherein the visual indication of the accumulated dose depicts the distribution of the accumulated dose with respect to the body of the patient.

8. The method of claim 1 wherein the visual indication of the reference dose levels comprises a color or grey-scale graphic on which the visual indication of the accumulated dose is superimposed.

9. The method of claim 1 wherein the visual indication of the accumulated dose of radiation and the visual indication of one or more reference dose levels are provided as a timeline.

10. The method of claim 1 wherein the visual indication of the accumulated dose of radiation represents the accumulated dose of radiation during the ongoing imaging operation in substantially real-time.

11. A method for conveying radiation dose information, comprising:
    estimating a dose of radiation to which a patient will be exposed based on a proposed set of image acquisitions, wherein each image acquisition gives rise to a separate image;
    displaying a visual indication of the estimate of the dose along with a visual indication of one or more reference dose levels; and
    updating the display of the visual indication of the estimate of the dose of radiation in response to changes made to the proposed set of image acquisitions.

12. The method of claim 11 wherein the changes made to the proposed set of image acquisitions comprise one or more of adding or removing image acquisitions from the proposed set of image acquisitions.

13. The method of claim 11 wherein the changes made to the proposed set of image acquisitions comprise altering one or more parameters associated with some or all of the image acquisition steps.

14. The method of claim 11 wherein the visual indication of one or more reference dose levels includes dose levels where the dose of radiation would be so low as to impair image quality.

15. The method of claim 11 wherein the visual indication of one or more reference dose levels includes dose levels where the dose of radiation would be so high as to trigger a reporting requirement.

16. The method of claim 11 wherein the visual indication of the estimate of the dose depicts a distribution of an accumulated dose with respect to the body of the patient.

17. The method of claim 11 wherein the visual indication of the reference dose levels comprises a color or grey-scale graphic on which the visual indication of the estimate of the dose is superimposed.

18. An imaging system comprising:
a source of radiation;
a detector on which radiation emitted by the source is detected and converted to signals;
a system controller controlling operation of one or both of the source and the detector;
a workstation in communication with the system controller, the workstation configured to display:
images reconstructed from the signals;
a visual indication of an accumulated dose of radiation administered during an ongoing imaging operation performed by the imaging system as the dose of radiation is accumulated; and
a visual indication of one or more reference dose levels.

19. The imaging system of claim 18 wherein workstation is further configured to display an estimated dose of radiation based on the ongoing imaging operation in conjunction with the visual indication of the accumulated dose and the visual indication of one or more reference dose levels.

20. The imaging system of claim 18 wherein the workstation is further configured to display a time remaining until the accumulated dose of radiation exceeds one of the one or more reference dose levels.

21. The imaging system of claim 18 wherein the workstation is further configured to display a visual representation of a body on which a distribution of the dose of radiation is displayed.

* * * * *